United States Patent [19]

Shibata

[11] Patent Number: 5,312,744
[45] Date of Patent: May 17, 1994

[54] METHOD OF IMMOBILIZING AND PRESERVING AN IMMUNOLOGICALLY REACTIVE SUBSTANCE

[75] Inventor: Yoichi Shibata, Tokyo, Japan
[73] Assignee: Olympus Optical Co., Ltd., Japan
[21] Appl. No.: 895,927
[22] Filed: Jun. 9, 1992

[30] Foreign Application Priority Data

Apr. 30, 1992 [JP] Japan ................................. 4-111848

[51] Int. Cl.$^5$ ...................... C12N 11/00; C12N 11/08; C12N 1/04; G01N 33/545
[52] U.S. Cl. .................... 435/174; 435/7.21; 435/177; 435/180; 435/181; 435/260; 436/518; 436/531; 436/532
[58] Field of Search .................. 435/181, 7.21, 174, 435/177, 180, 260; 436/532, 518, 531

[56] References Cited

U.S. PATENT DOCUMENTS

| | | | |
|---|---|---|---|
| 4,794,096 | 12/1988 | Parham et al. | 436/532 |
| 4,891,319 | 1/1990 | Roser | 435/188 |
| 5,030,560 | 7/1991 | Sinor et al. | 435/7.21 |
| 5,124,264 | 6/1992 | Imura et al. | 435/240.27 |

FOREIGN PATENT DOCUMENTS

| | | |
|---|---|---|
| 0140489A1 | 5/1985 | European Pat. Off. |
| 0317085A2 | 5/1989 | European Pat. Off. |
| 1257263 | 12/1971 | United Kingdom |

OTHER PUBLICATIONS

Immunochemistry, Pergamon Press 1969, vol. 6, pp. 67-76.

*Primary Examiner*—David M. Naff

[57] ABSTRACT

A method is provided for immobilizing and preserving an immunologically reactive antigen substance such as antigenic cells or non-cell bound antigens for use in solid-phase immunoassay. The antigen substance is adsorbed and crosslinked on a support and contacted with a protecting solution and containing sugar and an antiseptic substance such as NaN$_3$. The antigen substance is preferably centrifugally contacted with the support to shorten the time for adsorption. Crosslinking is with a solution of 1.0 to 5.0% formaldehyde or 0.003 to 0.06% glutaraldehyde. The antigenic cells can be a blood component such as platelets.

13 Claims, No Drawings

METHOD OF IMMOBILIZING AND PRESERVING AN IMMUNOLOGICALLY REACTIVE SUBSTANCE

BACKGROUND OF THE INVENTION

Field of the Invention

The present invention relates to a technique applied to the immunological survey of the cells that are important in view of clinical medicine, or more specifically to the method for preserving antigenic cells for solid-phase immunoassay that comprises immobilizing various antigenic cells onto a solid support like a reaction vessel for typing of the various antigenic types expressed on the antigenic cells and for detection of the existence of the antibodies that neutralize the antigens of the cells.

Description of the Related Art

A variety of blood components for transfusion and cells of organs for transplantation express various antigenic types. Hence, the cell having those antigens on the surface thereof is generally called as the antigenic cell. For the antigenic type which is expressed by those antigenic cells, before conducting transplantation or transfusion, the precise compatibility testing or neutralizing antibody confirmative assay is performed between a recipient and a donor. If, at that time, transplantation or transfusion is preformed, in spite of the insufficient compatibility or the existence of the neutralizing antibodies, it would expose a recipient to dangers such as serious rejection or GVH reaction. Accordingly, it is required, in the transfusion test, that the blood types of various blood cells such as red blood cells, platelets and white blood cells should be typed precisely with good reproduction. To meet this end, at present, the method is widely used where the presence of the antigen-antibody reaction is detected by contacting the blood cells whose blood type is known, with the blood sample from the patient. For using this method, it is necessary to assure a constant and stable supply of blood cells at any desired amount. For this purpose, the method has been applied where the maximum amount of available blood cells have been obtained in advance and preserved under freezing or cooling. However, the immunological effective span of living blood cells is 3–4 weeks, which is a short period, and with the passage of time, their antigenicity is remarkably lost. Hence, numerous trials have been practiced for stabilizing blood cells histologically.

Generally, in the passive (indirect) agglutination test and in the direct agglutination test, where red blood cells are precipitated as indicater cells and their distribution pattern is tested, a variety of aldehyde treatments have been preformed for stabilizing blood cells histologically.

In Immunochemistry, 6, 67, 1967, S. Avrameas et al., disclosed is the method to obtain the indicater cells for the passive agglutination test by stabilizing red blood cell surfaces histologically by treating with aldehyde sufficiently strong to lost their antigenicity, and then binding the antigens or antibodies for various pathogenic substances other than blood type ones, onto the red blood cell surface. Also, in European Patent Disclosure No. 317085, disclosed is the method to obtain the indicater cells for the direct agglutination test, whose antigens are histologically stabilized while the loss in antigenicity is minimized, by putting red blood cells to histrogical fixation with aldehyde at low concentration such as 0.01–2% formaldehyde (formalin) or 0.01–0.1% glutaraldehyde (glutar). The resulting indicater cells for the direct agglutination test are, for the purpose of maintaining their antigenicity, suspended in a complex protect solution comprising about a dozen of different component including gelatin or dextran, and preserved for 3 to 6 months under cooling.

It is possible to obtain the indicater cells comparatively stable in antigenicity by using those method, but even with those cells, the surface antigenicity is not completely free from inactivation. Further, the above indicater cells, because of their lacking ability for adsorbing antigens, requires a binder like tannic acid for immobilizing the antigens on the surface thereof. Furthermore, the antigens or antibodies that can be immobilized onto fine particles such as indicater cells are limited to those that have been made soluble by being subjected to sonication.

In recent years, the solid immunoassay, where immune reactive cells are adsorbed onto the microplate having multiple hollow wells thereupon and where a high sensitivity detection of the analyte in the sample from the patient is made possible, is going to form a main stream. In the solid phase method, it is important to bind a large amount of antigens to a solid support, and to maintain the activity of those antigens, and for that purpose, a variety of devices have been introduced as given below.

In the European Patent Disclosure No. 140489, disclosed is the method where solutions each containing a single kind of antigens such as hormones or immunoglobulins are poured into individual wells on the polyvinyl chloride microplate, the antigens are allowed to be adsorbed thereon with physical adsorption force and then to contact with solutions containing various sugars, and left to be dried. As an alternative, in U.S. Pat. No. 4,891,319 disclosed is the method where the anti-leukocyte antibodies or enzymes to a single kind of antigens are poured to each well of the polystylene microplate, left to stand for a long period for physical adsorption, allowed to contact with a trehalose solution, and left to be dried. However, the cells immobilized only with physical adsorption force has a problem being ready to peel off during preservation or reaction processes.

Further, in U.S. Pat. No. 5,030,560, disclosed is the method where, for preventing the inactivation of the antigenicity on the surface of red blood cells with aldehyde treatment, the antigenic blood cells such as red blood cells or platelets are allowed to be immobilized on the microplate for solid immunoassay through a dye with positive charges as a binder, to contact with various sugar solutions and left to be dried. However, when the adsorption of such a charged binder is used, the antigenic blood cells bind non-specifically to various proteins other than the analyte, which may lead to mistyping of the result.

By the way, the present inventor, with an intention to realize the typing of antigens to platelets that has been craven for, developed the anti-platelet antibody test kit that is based on the mixed passive hemagglutination (MPHA) that depends on the usage of the microplate on which platelets have been immobilized only with physical adsorption force, and of the indicater cells which is obtained by binding anti-IgG antibodies to sheep red blood cells. This kit is marketed under the trade mark of OLYBIO and contributes to the research in the field of the transfusion test. However, while this kit is free from the problem involved in the inactivation of antigenicity because the platelets being immobilized to the plate only with the physical adsorption of the plate itself, the platelets are not necessarily immobilized to the plate with a sufficient binding force.

Although various studies have been tried as described above, no method of immobilizing antigenic blood cell has been proposed that is excellent in reaction specificity and in adsorption to the microplate, and allows the stable maintenance of antigenicity over a long period. Further, a majority of the researches regarding the maintenance of antigenicity use red blood cells as their material, and in spite of the importance in terms of transfusion, the case where a large number of antigen types in platelets are maintained stable over a long period has never been presented.

SUMMARY OF THE INVENTION

With above situations as a background, the first object of the present invention is to provide the method for preserving antigenic cells for solid immunoassay, where the cells are excellent in adsorption on a solid support and the specific binding activity to the analyte is maintained stably over a long period. The second object is to provide the method for preserving the antigenic cells for solid immunoassay that allows multiple antigenic types in platelets to maintain activity stably over a long period.

To solve these problems, this invention adopts the method to immobilize antigenic cells by choosing a most appropriate combination of the binding forces with physical adsorption and chemical crosslinking and to contact the antigenic cells with a protect solution.

To put it more specifically, according to this invention, provided is a method for preserving an immunologically reactive substance immobilized on a surface of a solid support to operate an immunological study comprising;

first binding process for adsorbing said reactive substance on a surface of said support by the physical adsorption treatment, a second binding process for forming a bridged linkage between said reactive substance and said support by the chemical crosslinking treatment so that the chemical crosslinking cooperates with the physical adsorption for enough strong immobilization and leaves the complete antigenicity, and a immersing process for protecting said reactive substance immobilized on said support from a structual damage with a protect solution containing at least of an effective amount of sugar.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

DETAILED DESCRIPTION OF THE PREFERRED EMBODIMENTS

The detailed description of this invention will be given below. In the present invention, immunologically reactive substance is typically an antigenic cell, but not limited to the antigenic cell, other immunologically reactive substance may be used including non-cell bound antigens. The following detailed description is an embodiment of the present invention for antigenic cell.

Firstly, as a preliminary for the execution of the method of this invention, antigenic cells are bound to a solid support with physical adsorption treatment.

The antigenic cells to be used for this invention can include all cells that express antigens having the immunological activity on the cell surface. For example, the cells of the internal organs such as bone marrow, spleen, kidney, liver, endothelium, cornea, malignant tumor, human hair, and the cells constituting blood components such as platelets, red blood cells, white blood cells, can be used. Further, the culture, homogenate or lysate prepared from them can be used effectively.

When the antigenic cells of this invention are red blood cells or platelets that have known antigen types, normally a type O blood sample is used for preventing the occurrence of non-specific reactions among antigens of different ABO blood types. Further, when the test object concerns with a specific antigen type peculiar to platelets, it is preferred to use the antigenic cells in which the HLA antigens on the cell surface have been inactivated. Otherwise, it may lead to mistyping because of the HLA antibodies in the sample from the patient also react with the active HLA antigen under study. Furthermore, for refining platelets from blood, the use of blood left 30 minutes or more after collecting prevents the sample from being contaminated with red blood cells during centrifugation. The solid support to be used for this invention can take any form if it has hollow parts in which a test sample or a reagent can be poured, or surfaces which can be immersed in a test sample or a reagent. To put it more specifically, for example, reaction vessels such as microplates, test tubes, box form curvettes or laboratory test tools such as glass slides, filters, fibers, tubular flow cells can be used. Surface configuration of those solid support can be modified according to the properties of the antigen to be immobilized, the characteristic to be tested, or the reagents for test. When, for example, the precipitated indicater cells are used as a reagent, the reaction vessel having a U- or V-shaped base can be preferably used, and what is particularly preferable is microplates. Further, in the tests where color reactions or luminous reactions are used, any testing tool can be used, no matter what form its surface may have.

The material of the solid support for this invention should have a physical adsorption. To put it specifically, for example, plastics such as polystylene, polyethylene or polyvinyl chloride can be preferably used. The ordinary material to which has been conferred physical adsorption by certain electrical, physical or chemical treatments can also preferably be used. For example, a glass surface can be used by coating a well-known positive charged substance such as poyethylene imine (PEI), polyvinyl pyrrolidone (PVP) or a cation dye, or a well-known negative charged substance such as vegetable gum, starch, sodium alginate, gelatin thereupon. Furthermore, it is possible to reinforce the physical adsorption activity of the above plastic wares by treating them with those substances. For example, the microplates whose physical adsorption activity at their U-shaped, polystyrene wells is reinforced, include the module plates from NUNC Inc. such as Maxisorp (IgG binding activity being 400 ng/cm$^2$) and Polysorp (100 ng/cm$^2$ IgG), or those from Greiner Inc. such as Immuron 600 (600 ng/cm$^2$ IgG) and Immuron 200 (200 ng/cm$^2$ IgG).

The treatment of the solid support by those substances should not be performed at such a high concentration as to possibly interfere with the results after Immobilization. The material of the support or the kind of the charged adsorbent substance mentioned above are suitably changed, according to the adsorption properties of the antigenic cell themselves to be immobilized or the amount of the cell.

The physical adsorption treatment in this invention can be achieved by contacting a cell suspension having an effective amount of antigenic cells suspended, with a solid support, and leaving the assembly at room temperature for a predetermined period or submitting it to high speed centrifugation. The effective amount of antigenic cells for immobilization contains so many cells as to permit at least one layer of antigenic cells to be formed upon the surface of the solid support. Because such effective amount varies depending on the kind and nature of the antigen to be immobilized, or the physical adsorption properties or the solid phase area of the solid support, it is recommended to choose appropriate cell concentrations and addition amounts by varying the related conditions as appropriate. Particularly when it is desired to effect physical adsorption in a short time, it is preferred to resort to high speed centrifugation.

The solution where the antigenic cells of this invention are suspended may be selected as appropriate from among those well known in accordance with the characteristics of the cells to be immobilized. Specifically, for example, various buffers or physiological saline can be used. Further, the particularly preferable solution to be used for suspending platelets in this invention is ACD solution. After treatment, the support should be washed as needed with an appropriate washing solution such as purified water, buffer, saline or blood dilution.

After this physical adsorption treatment, the chemical crosslinking treatment is applied to the solid support to which the above antigenic cells have been bound.

This sequence should be followed because if the chemical crosslinking were processed at the same time with or before physical adsorption treatment, chemical crosslinking would proceed at first within antigenic cells, thus the physical adsorption or chemical crosslinking to the solid support will not be carried out sufficiently.

The chemical crosslinking treatment of this invention is performed by dissolving a chemically crosslinking agent into a suitable buffer or saline and contacting the solution with the solid support on whose surface antigenic cells have been immobilized.

Any chemical crosslinking agent can be used for this invention, as for example, a carboxylic acid, an epoxy compound, a halogen compound, an acid anhydride, a silane compound, an isocyanate, an alcohol or an amine, which acts mainly on a hydroxyl group or a double bond, unless it has in itself a potency eliciting antigent-antibody reaction, nor has adsorption activity ascribed to its electric charge. It is preferred, however, to use aldehyde-based chemical substances such as formalin, glutar (glutaraldehyde) or paraformaldehyde. This is because they allow, together with reinforcement of the binding of antigenic cells to the solid support, histological immobilization of those antigenic cells. Particularly preferable is glutaraldehyde. The use concentration of those aldehyde-based substances varies depending on the characteristics of the substances to be used. When a formalin-containing solution is used, it is preferred to select such a concentration as to permit the final concentration to be at 1.0–5.0%. If the concentration exceeds 5.0%, the antigenicity is lost, and, after immobilization, the antigenic cells are often subject to non-specific reactions due to aldehyde. On the other hand, if the concentration is less than 1.0%, parts of cells will peel off from the surface of the well during wash, protection treatment or preservation. What is more preferable is a range between 2.5 and 4.5%. When a glutar containing solution is used, its effective glutar concentration is preferably at a range of 0.003–0.06%. If the concentration is less than 0.003%, the fixation force will be greatly reduced, while if the concentration exceeds 0.06%, the antigenicity will be lost. What is more preferable is a range of 0.005–0.02%. It is possible to maintain stable and economical immobilization by adjusting as appropriate the concentration of aldehyde in accordance with the physical adsorption force of the solid support under study, as long as the above effective concentration range of aldehyde is used.

Further, a mixture comprising several aldehyde substances can effectively be used in accordance with the object of the study. In this case, it is desirable to determine the optimum range for concentration before use. Whether a given aldehyde concentration is adequate or not, can be determined by checking in a washing solution after the treatment, or in a protect solution to be added after washing, for the floating of the cells that should have been immobilized. In the case of immobilizing a compound having a low molecular weight such as synthetic peptide or hapten, it is needed that the concentration of a crosslinking agent will be high, because it is difficult to use physical adsorption.

The methods by which to contact the thus obtained solution with a solid support are ones to preferably pour the solution with a pipette onto the solid support or to immerse the solid support into the solution. When those methods are put into practice, care should be taken to make it as gently as possible. This is because otherwise cells may be peeled off by the liquid current. The contact temperature is preferably at 4°–37° C. The contact time is preferably 10–50 minutes, or more preferably 20–40 minutes. This is because, if the contact time is too long, histological fixation of antigenic cells will proceed more than needed, or the antigenicity will be lost. Hence, it is necessary to wash the solid support with an appropriate washing solution immediately after a predetermined period. As a result, the antigenic cell are immobilized firmly, whose antigenicity is completely maintained.

In the present invention, the antigenic cells on a solid support treated by a chemical crosslinking treatment described above are allowed to contact with a protect solution, to achieve stable preservation of the antigenic cells over a long period.

For the protect solution to be used for this invention, any solution containing sugars and additives may be used. Any sugar can be preferably used such as monosaccharides, polysaccharides, sugar alcohol. Particularly preferably, saccharose, lactose or dextran can be used in view of economy and availability. These sugars form a protection membrane on the surface of antigenic cells immobilized on a support and prevent the antigenic cells effectively from the structural damage during the preservation, for example, under freezing.

For the solvent that dissolves the above sugars, any one that does not affect the physicochemical nature of the cells may be used. However, a buffer with a buffer activity sufficiently weak not to affect the physicochemical nature of the cells, or physiological saline may be preferably used. The content of the above sugars to the solvent is preferably 0.5-10%. Particularly, 1-5% is more preferable in view of economy and preservation stability.

For the additive to be used for the present invention, any known additive can be used. However, for example, serum albumin, gelatin, sodium azide are preferably used. Of those, antiseptic substances such as sodium azide are most preferred. The concentration and volume of various additives in a protect solution are preferably determined as appropriate in accordance with the kind and volume of the cells to be preserved.

As an example of the protect solution to be used for this invention, sterilized saline comprises 1% saccharose and 0.1% $NaN_3$ may be used. The protect solution comprises effective compositions capable of meeting economy and preservation purposes at the same time. The effective range in concentration of sugar and $NaN_3$ of this solution is 1-8% and 0.01-0.5%, respectively.

After the thus obtained solution has been allowed to contact with the cells, the assembly is incubated at 4°-37° C. for an appropriate time. This treatment allows the sugar component in the protect solution to penetrate spaces between the molecules of the cells, thereby preventing the denaturation of the physicochemical characteristics of the cells.

In the present invention, the preservation method after the cells and the protect solution have been contacted each other, are those to preserve the solid support on which the cells are immobilized, in a protect solution, or to dry the support for preservation.

The temperature for preserving the support in a protect solution is preferably at −5° to 10° C., or most preferably at 4° C. Accordingly, the support should be preferably preserved under cooling or freezing. When the support is preserved in a protect solution, care should be taken not to allow vaporization or leak to occur during preservation. This is because as the volume of the protect solution changes, its concentration varies so that its reactivity becomes irregular. For preventing the vaporization and leakage, it is advisable to seal the support into an air-tight box with a damp cloth.

The drying methods for preserving the support by drying are natural drying or drying under depression, and either one can be preferably used, but natural drying is more preferred. Any temperature may be chosen for the temperature necessary for preserving the solid support after natural drying, as long as no thermal denaturation occurs in the cells on the support, but the support should be preferably preserved at room temperature. When the support is preserved under drying, it is important to prevent it from the exposure to oxidating atmosphere and moisture. Accordingly, it is preferred to act a desiccant on it, or keep it in a pack filled with a dehumidified gas or in vacuum packing.

Regardless which method is adopted for preservation, in order to eliminate defects of each method effectively, it is preferred to seal the solid support with an appropriate sealing material, and to keep the support in a place that is little subject to temperature changes. Particularly when the microplate is used as a solid support, the seal specially made for the plates can be preferably used. Especially, when the module plate comprising a small number of wells such as 8×1 or 8×2 is used, it is preferred to use the caps specially made for it. This is because the portability and handiness are significantly improved by sealing the support with the caps.

The antigen-immobilized solid support treated in accordance with the above preservation conditions can maintain immobilization condition and antigenicity practically permanently in a protect solution or under drying.

Below wil be given an example of the use for solid immunoassay of the immobilized cells preserved in accordance with the method of this invention.

The sealing or cap applied to the solid support is removed, and the support is washed thoroughly with a washing solution containing a surfactant such as Tween 20. With this washing treatment, it is possible to effectively remove the excess attachments resulting from disintegration or peeling-off during preservation, or the detachments of the antigenic cells that occur as a result of rough treatment or insufficient immobilization. In addition, this treatment prevents the support from the charge of static electricity that may interfere with the integrity of the immobilized part of the support.

The washed solid support is allowed to contact with the sample from the patient to be studied such as serum, plasma or whole blood, and the assembly is incubated at 37° C. for a period necessary for a given reaction. Through this process, various antigens on the cell surface overlying the solid support bind with the antibodies in the sample specific to said antigens. Generally, after the reaction, the support is put to washing treatment for removing the portion not undergoing reaction, but such washing treatment is not necessary for the homogenous reaction system.

Then, the support is incubated together with a complex of a substance that has a specific affinity to a part or the whole type of antibodies and a marker substance. Anti-immunoglobulin antibodies can be used as a substance that has a specific affinity to a part or the whole type of antibodies. The immunoglobulin type of the antibodies to be used here should be the same with that of the antibodies from the sample. The marker substance can be selected from a group of substances which themselves can be counted objectively such as magnetic substances, fluorescents, radioisotope or visible particles and, color substances or luminous substances which react with substrates or catalysts. The temperature for incubation is preferably at room temperature to 37° C. When anti IgG antibodies are used, the reaction gets saturated in 4 hours, but it requires a further time for its pattern to be stabilized. Thus, it is preferable to allow the reaction to proceed overnight.

After incubation, the solid support from which the unreacted portion has been removed through washing is used to detect the presence of the marker substance and the number thereof. Appropriate known methods can be applied for the detection. Particularly when the maker substance is a visible particle whose diameter is within the range of of 2-10 $\mu$m, the qualitative analysis test can be macroscopically performed.

Examples of this invention will be detailed below, but the scope of the present invention is not limited to them.

(Example 1) Immobilization based on the usage of formalin and its preservation effects (1) Preparation of platelet-immobilized plates Volumes of whole blood sampled from each of 9 donors (all the blood being of type O) and 1 volume of ACD solution were mixed, and each of the resulting mixed solution was centrifuged at 260 xg to obtain plate rich plasma (PRP). To 9 volume of PRP obtained thus, was added a further one volume of ACD solution, and the mixture was centrifuged at 1,100 xg to obtain platelet concentrate (PC). The thus obtained PC was washed with physiological solution (saline), and left in PBS-EDTA solution containing 29% (w/v) chloroquine (pH 5.0) at room temperature for 30 minutes, to inactivate HLA antigens being washed with saline, adjusted with saline to $8 \times 10^4$ cells/μl, and the resulting suspension was poured to the U-based microplates (Nunc, module type, Maxisorp) at 50 μl/well. After the assembly was centrifuged at 670 xg, the PBS solution (pH 6.7) containing formalin of various concentrations was gently added to each well at 100 μl/well. Immediately after having been left at room temperature for 20 minutes, the assembly was washed with saline, and here resulted the microplates upon which platelets were immobilized to a necessary degree. To the thus obtained plates was added saline containing 1% saccharose and 0.1% $NaN_3$ as a protect solution at 50 μl/well. The resulting microplates were preserved in two different ways. Namely, the one half of the plates were each sealed as they were, and preserved in a refrigerator at 4° C. for 15 months. The other half, after having had been dried naturally at 37° C. for 24 hours, was sealed in an aluminum bag together with a desiccant, and preserved at room temperature for 6 months.

(2) Detection of anti-platelet antibodies.

The platelet-immoblized plates, after having had been preserved by the above two different methods, had their seal opened, and were thoroughly washed with saline containing 0.05% Tween 20. After the saline being removed, the same washing solution was poured in to the plates at 25 μl/well. The serum preparations each containing the antibodies corresponding with the antigens to be studied were diluted about 4-fold with saline. Those were submitted to ultra-high centrifugation at 3,000–10,000 r.p.m., through which precipitating components such as debris and fibrin were precipitated. The resulting supernatants each were poured to the plates at 25 μl/well. The plates were shaked lightly to allow the reaction to proceed at room temperature for 3 hours. The plates were washed with saline containing 0.05% Tween 20, and, after the saline being removed, the same washing solution was poured to the plates at 25 μl/well. The indicater cell suspension (Olympus Optical Co.) containing sheep red cells covered with anti human IgG was poured to the plates at 25 μl/well and left at room temperature overnight for reaction. The reaction pattern appearing on the well bases after overnight incubation was examined macroscopically. During each of the reaction processes, the microplates were kept in a humidor box in which a towel humidified with saline containing 0.05% Tween 20 was put, to prevent evaporation effectively therefrom. In Table 1 below, shown is the reactivity of the microplates, after preserving the microplates immobilized with PBS solution (the final formalin concentration being 4.7%) containing 7% formalin.

When the well bases of a microplates were observed, the distribution pattern showing indicater cells uniformly bound all over the well was taken as positive (+), while the distribution pattern giving a majority of indicater cells precipitated at the center of the well was taken as negative (−). The (NT) in the table means no antigen being detected. As a control, shown is the reactivity of the microplates after preserving the microplates immobilized by only conventional adsorption where no aldehyde was used.

TABLE 1

| Antiserum | No. 1 Conventional method | 4° C. | Dried | No. 2 Conventional method | 4° C. | Dried | No. 3 Conventional method | 4° C. | Dried |
|---|---|---|---|---|---|---|---|---|---|
| HPA-1a(pl[A1]) | + | + | + | + | + | + | − | − | − |
| -1b(pl[A2]) | − | − | − | − | − | − | + | + | + |
| HPA-2a(Ko[b]) | + | + | + | − | − | − | + | + | + |
| -2b(Sib[a]) | − | − | − | + | + | + | − | − | − |
| HPA-3a(Bak[a]) | − | − | − | + | + | + | + | + | + |
| -3b(Bak[b]) | + | + | + | + | + | + | + | + | + |
| HPA-4a(Yuk[b]) | − | − | − | + | + | + | + | + | + |
| -4b(Yuk[a]) | + | + | + | − | − | − | − | − | − |
| HPA-5a(Br[b]) | + | + | + | + | + | + | + | + | + |
| -5b(Br[a]) | − | − | − | − | − | − | + | + | + |
| Nak[a] | + | + | + | + | + | + | + | + | + |

| Antiserum | No. 4 Conventional method | 4° C. | Dried | No. 5 Conventional method | 4° C. | Dried | No. 6 Conventional method | 4° C. | Dried |
|---|---|---|---|---|---|---|---|---|---|
| HPA-1a(pl[A1]) | NT | NT | NT | NT | NT | NT | NT | NT | NT |
| -1b(pl[A2]) | NT | NT | NT | NT | NT | NT | NT | NT | NT |
| HPA-2a(Ko[b]) | + | + | + | + | + | + | + | + | + |
| -2b(Sib[a]) | − | − | − | − | − | − | − | − | − |
| HPA-3a(Bak[a]) | + | + | + | + | + | + | + | + | + |
| -3b(Bak[b]) | NT | NT | NT | NT | NT | NT | NT | NT | NT |
| HPA-4a(Yuk[b]) | NT | NT | NT | NT | NT | NT | NT | NT | NT |
| -4b(Yuk[a]) | NT | NT | NT | NT | NT | NT | NT | NT | NT |
| HPA-5a(Br[b]) | − | − | − | + | + | + | + | + | + |
| -5b(Br[a]) | + | + | + | − | − | − | − | − | − |
| Nak[a] | NT | NT | NT | NT | NT | NT | NT | NT | NT |

| Antiserum | No. 7 Conventional method | 4° C. | Dried | No. 8 Conventional method | 4° C. | Dried | No. 9 Conventional method | 4° C. | Dried |
|---|---|---|---|---|---|---|---|---|---|
| HPA-1a(pl[A1]) | NT | NT | NT | NT | NT | NT | NT | NT | NT |
| -1b(pl[A2]) | NT | NT | NT | NT | NT | NT | NT | NT | NT |
| HPA-2a(Ko[b]) | + | + | + | + | + | + | + | + | + |
| -2b(Sib[a]) | − | − | − | − | − | − | − | − | − |
| HPA-3a(Bak[a]) | + | + | + | + | + | + | − | − | − |

TABLE 1-continued

| | | | | | | | | | |
|---|---|---|---|---|---|---|---|---|---|
| -3b(Bak[b]) | NT | NT | NT | NT | NT | NT | NT | NT | NT |
| HPA-4a(Yuk[b]) | NT | NT | NT | NT | NT | NT | NT | NT | NT |
| -4b(Yuk[a]) | NT | NT | NT | NT | NT | NT | NT | NT | NT |
| HPA-5a(Br[b]) | + | + | + | + | + | + | + | + | + |
| -5b(Br[a]) | − | − | − | − | − | − | − | − | − |
| Nak[a] | NT | NT | NT | NT | NT | NT | NT | NT | NT |

As shown in Table 1 above, the antigenicity of various antigens of platelets from 9 persons did not show any change after preservation. Particularly, for the antigenic type, HPA 2a, HPA-2b, HPA-5a and HPA-5b whose antigenicity has been considered weak, their antigenicities could be maintained for a long period. Thus, this method will be greatly useful for the transfusion test in which platelets having those antigenic types are used. Further, even if platelets, after having been immobilized, are submitted to drying treatment, their antigenicity does not change. This makes it possible for platelets to be preserved at room temperature for a remarkable long time.

By comparing the results that were derived when the concentrations of the formalin to be added were varied, it was found that the effective range of the final concentration of formalin in a well is at 1.0-5.0%. If the concentration exceeds this range, the antigenicity is lost, while if the concentration is lower than 1.0%, parts of the cells tend to be peeled off from the well surface during washing, protection treatment or preservation. The final concentration of formalin avoiding exactly such inconveniences lies at 2.5-4.5%.

In correlation with the concentration of formalin to be added, an expansion of indicater cells that may result from non-specific reactions was observed in the distribution pattern proved to be negative. When the types of the microplates changed to the one having a lower binding activity (Nunc, Polysorp), the effective PC concentration was found to be 150,000 cells/μl. The addition concentration of PC to the microplats whose physical adsorption are different, is from 50,000 to 200,000 cells/μl.

(Example 2) Immobilization based on the usage of glutar and its preservation effect Platelets sampled from 3 donors (all the blood being of type O) different from the 9 donors in Example 1 were treated in the same manner as in Example except that aldehyde to be added was substituted for glutar.

In Table 2 below, the reactivity of the microplates are indicated after preserving the microplates immobilized with PBS solution containing 0.02% glutar. The criterion and the point being compared with the conventional method are the same as those of Example 1.

As shown in Table 2 above, various platelet antigens from the platelets of the 3 donors, are stabilized over a long period by the immobilization treatment with glutar and do not show any change in their antigenicity before and after preservation.

As contrast with the cases where formalin was used, in the reaction results obtained by using the plates immoblized with glutar, no expansion of indicater cells resulting from non specific reactions was observed in the plates immobilized with gultar. Further, from the results of platelet-immobilized plates which were obtained at the different concentration of glutar in PBS solution, it was found that when the glutar concentration in PBS solution is less than 0.003%, the fixation force is significantly reduced, while when it exceeds 0.06%, the antigenicity tends to be lost. From this, it was concluded that the final concentration of glutar, after being added to the preparation, should be 0.003-0.06% to be effective, or more preferably be 0.005-0.02%

(3) Investigation of the composition of the protect solution

The composition of the protect solution was investigated. To each well of the platelet-immobilized microplate that had been treated in the same manner as in Examples 1 and 2, added was a protect solution that had been prepared by combining sterilized saline and a plural kinds of sugar solutions, which were conventional ones, and the assembly was preserved at 4° C. over a long period. After the lapse of a predetermined period, the plate was taken out, and treated in the same manner as above to check whether the antigenicity lowered or not. The results are shown in Table 3 below.

TABLE 3

| Composition of protect solution | Antigenicity after preserved | |
|---|---|---|
| | After 3 weeks | After 18 months |
| Sterilized saline | Inactivation depression | |
| Sterilized saline containing 1% saccharose | | |
| Sterilized saline containing 1% saccharose and 0.1% NaN$_3$ | No change | No change |

TABLE 2

| | No. 1 | | | No. 2 | | | No. 3 | | |
|---|---|---|---|---|---|---|---|---|---|
| Antiserum | Conventional method | 4° C. | Dried | Conventional method | 4° C. | Dried | Conventional method | 4° C. | Dried |
| HPA-1a | + | + | + | + | + | + | + | + | + |
| -1b | − | − | − | − | − | − | − | − | − |
| HPA-2a | + | + | + | + | + | + | + | + | + |
| -2b | − | − | − | − | − | − | − | − | − |
| HPA-3a | + | + | + | + | + | + | + | + | + |
| -3b | + | + | + | + | + | + | + | + | + |
| HPA-4a | + | + | + | + | + | + | + | + | + |
| -4b | − | − | − | − | − | − | − | − | − |
| HPA-5a | + | + | + | + | + | + | + | + | + |
| -5b | − | − | − | − | − | − | − | − | − |
| Nak[2] | + | + | + | + | + | + | − | − | − |

TABLE 3-continued

| Composition of protect solution | Antigenicity after preserved | |
|---|---|---|
| | After 3 weeks | After 18 months |
| Sterilized saline containing 1% lactose and 0.1% NaN₃ | No change | No change |

As evident from Table 3 above, the antigen-immobilized plate prepared by the immobilization method of this invention can be preserved over a long period in a protect solution having a very simple composition. Further, when the saccharose concentration in the protect solution was varied, it was found that the effective range of the sugar to be put into the protect solution is at 0.5-10%. When saccharose was replaced with lactose, the same preservation stability was obtained. Further, when the protect solution was so simplified as to comprise only sugars and an antiseptic substances, it was found that the antigenicity and adsorption activity did not undergo any change even after 15 months. From this, it will be safe to say that the immobilized plate prepared in accordance with the present invention can be preserved practically permanently to be ready for use at any time in the meantime.

In Example 3, NaN₃ was used, but if other various additives are added together to the protect solution, the same preservation stability could possibly be obtained.

The preservation method of this invention, because it combines the physical adsorption treatment and chemical crosslinking treatment in a proper manner, allows antigenic cells to bind more firmly to a solid support than the method solely dependent on physical adsorption for immobilization, and it also allows the prevention of non-specific reactions that may take place when only physical adsorption is enhanced. Further, the present method, by treating the preparation with aldehyde of a proper concentration, can improve the histological stability of antigenic cells while effectively preventing the destruction and decline of the antigenicity.

The preservation method of this invention can stably maintain the antigenicity, even when the activity of various antigens related with platelets varies according to their types. Accordingly, when immobilized cells preserved by the present preservation method are used, reliable test results can always be obtained. The immobilized cells in the present method are firmly immobilized and histologically stable, so that it is possible to preserve them in a simple protect solution or at dried state over a long period. This is also economically very advantageous.

Additional advantages and modifications will readily occur to those skilled in the art. Therefore, the invention in its broader aspects is not limited to the specific details, and illustrated examples shown and described herein. Accordingly, various modifications may be made without departing from the spirit or scope of the general inventive concept as defined by the appended claims and their equivalents.

What is claimed is:

1. A method for immobilizing and preserving an immunologically reactive antigen substance on a surface of a solid support comprising:
   (a) centrifugally bringing a suspension of immunologically reactive antigen substance selected from the group consisting of antigenic cells and non-cell bound into contact with a surface of a solid support having physical adsorption capability so as to permit the antigen substance to be immobilized on the solid support by means of physical adsorption;
   (b) bringing a 1.0 to 5.0% formaldehyde solution or a 0.003 to 0.06% glutaraldehyde solution into contact with the antigen substance immobilized by physical adsorption on the solid support so as to more strongly bond the antigen substance on the solid support while maintaining the antigenicity of the immobilized antigen substance;
   (c) washing the solid support with a washing solution capable of inhibiting further action performed by the formaldehyde or the glutaraldehyde; and
   (d) contacting the immobilized antigen substance on the solid support with a protecting solution itself containing 0.5 to 10.0% of sugar and a suitable amount of antiseptic substance so as to protect the antigen substance immobilized on the solid support from structural damage.

2. A method according to claim 1, wherein the formaldehyde solution has a formaldehyde concentration of 2.5 to 4.5%.

3. A method according to claim 1, wherein the glutaraldehyde solution has a glutaraldehyde concentration of 0.005 to 0.02%.

4. A method according to claim 1, wherein said protecting solution contains at least one sugar selected from the group consisting of saccharose, lactose and dextran.

5. A method according to claim 1, wherein the antiseptic substance is NaN₃.

6. A method according to claim 1, wherein the antigen substance is composed of a constituent blood component.

7. A method according to claim 6, wherein the blood component is blood platelets.

8. A method according to claim 7, wherein the blood platelets carry an antigen selected from the group consisting of HPA-2a, HPA-2b, HPA-5a and HPA-5b.

9. A method according to claim 7, wherein the blood platelets are suspended in the suspension in a concentration of 50,000 to 200,000 cells/μl.

10. A method according to claim 1, wherein the solid support is provided with a recess capable of housing all of the suspension containing the antigen substance and the formaldehyde or glutaraldehyde solution.

11. A method according to claim 10, wherein the solid support is a micro titer plate having a U or V shaped bottom surface.

12. A method according to claim 1, further comprising storing the support containing the immobilized antigen substance at 4° C.

13. A method according to claim 1, further comprising drying the solid support containing the immobilized antigen substance.

* * * * *

UNITED STATES PATENT AND TRADEMARK OFFICE
CERTIFICATE OF CORRECTION

PATENT NO. : 5,312,744
DATED : May 17, 1994
INVENTOR(S) : Shibata, Yoichi

It is certified that error appears in the above-indentified patent and that said Letters Patent is hereby corrected as shown below:

In column 1, line 61, change "lost" to --lose--;

In column 2, line 1, change "histrological" to --histological--;

lines 24, 25, change "is going to form a main stream" to --has become an important procedure.--;

line 62, change "craven for" to --long sought after--;

line 66, change "is" to --are--;

In column 3, line 50, change "a" to --an--;

In column 5, line 57, change "nor" to --or--;

In column 6, line 44, change "proceed than" to --proceed further than--;

line 62, change "prevent" to --protect--;

In column 7, line 28, change "method" to --methods--;

line 30, change "each" to --with each--;

line 53, change "oxidating" to --oxidizing--;

line 55, change "to act a desiccant on it" to --to expose it to a desiccant--;

UNITED STATES PATENT AND TRADEMARK OFFICE
CERTIFICATE OF CORRECTION

PATENT NO. : 5,312,744
DATED : May 17, 1994
INVENTOR(S) : Shibata, Yoichi

It is certified that error appears in the above-indentified patent and that said Letters Patent is hereby corrected as shown below:

In column 8, line 67, change "plate" to --platelet--;

In column 9, line 7, change "antigens being" to --antigens of PC. The HLA antigen-inactivated PC was, after being--;

line 33, change "being" to --was--;

In column 10, line 9, change "being" to --was--;

line 31, change "being" to --was--;

In column 11, line 47, change "Example" to --Example 1--;

In column 12, lines 36 & 37, change "a plural kinds" to --a plurality of--;

line 45, change "18" to --15--;

UNITED STATES PATENT AND TRADEMARK OFFICE
CERTIFICATE OF CORRECTION

PATENT NO. : 5,312,744
DATED : May 17, 1994
INVENTOR(S) : Shibata, Yoichi

It is certified that error appears in the above-indentified patent and that said Letters Patent is hereby corrected as shown below:

In column 13, line 20, change "substances" to --substance--;

In column 14, line 3, change "support" to --support,--;

line 7, change "bound" to --bound antigens--.

Signed and Sealed this

Fifteenth Day of November, 1994

Attest:

BRUCE LEHMAN

Attesting Officer

Commissioner of Patents and Trademarks